(12) United States Patent
Kim et al.

(10) Patent No.: US 8,865,933 B2
(45) Date of Patent: Oct. 21, 2014

(54) METHOD FOR OBTAINING OPTICALLY PURE AMINO ACIDS

(75) Inventors: Kwan-Mook Kim, Seoul (KR); Hojun Kim, Seoul (KR)

(73) Assignee: Aminologics Co., Ltd., Seoul (KR)

( * ) Notice: Subject to any disclaimer, the term of this patent is extended or adjusted under 35 U.S.C. 154(b) by 204 days.

(21) Appl. No.: 13/258,948

(22) PCT Filed: Mar. 19, 2010

(86) PCT No.: PCT/KR2010/001707
§ 371 (c)(1),
(2), (4) Date: Sep. 22, 2011

(87) PCT Pub. No.: WO2010/110555
PCT Pub. Date: Sep. 30, 2010

(65) Prior Publication Data
US 2012/0016157 A1   Jan. 19, 2012

(30) Foreign Application Priority Data
Mar. 23, 2009   (KR) .................. 10-2009-0024287

(51) Int. Cl.
C07C 229/00 (2006.01)
C07C 227/34 (2006.01)
C07D 209/20 (2006.01)
C07C 273/16 (2006.01)
C07B 55/00 (2006.01)
C07C 227/36 (2006.01)
C07C 319/28 (2006.01)
C07B 57/00 (2006.01)

(52) U.S. Cl.
CPC ............ *C07C 273/16* (2013.01); *C07C 227/34* (2013.01); *C07D 209/20* (2013.01); *C07B 55/00* (2013.01); *C07C 227/36* (2013.01); *C07C 319/28* (2013.01); *C07B 2200/07* (2013.01); *C07B 57/00* (2013.01)
USPC ........................................................ 562/433

(58) Field of Classification Search
None
See application file for complete search history.

(56) References Cited

U.S. PATENT DOCUMENTS

| 5,266,468 A | 11/1993 | Miller | |
|---|---|---|---|
| 7,268,252 B2 * | 9/2007 | Kim et al. | ..................... 562/553 |
| 2009/0023931 A1 | 1/2009 | Mook et al. | |

FOREIGN PATENT DOCUMENTS

| JP | 5-70415 A | 3/1993 |
|---|---|---|
| KR | 10-2006-0088489 A | 8/2006 |
| KR | 10-2008-0093437 A | 10/2008 |
| KR | 10-0870227 B1 | 11/2008 |

OTHER PUBLICATIONS

Tang et al., Tetrahedron Letters 49 (2008) 6917-6916.*
Tang et al., J. Org. Chem., 2008, 73, 5996-5999.*
Park et al., J. Am. Chem. Soc., 2007, 129 (6), 1518-1519.*
Olivard et al., The Journal of Biololical Chemistry, 1952, 669-674.*

(Continued)

*Primary Examiner* — Karl J Puttlitz
(74) *Attorney, Agent, or Firm* — Dickstein Shapiro LLP

(57) ABSTRACT

This invention relates to a method for obtaining optically pure amino acids, including optical resolution and optical conversion. This method significantly shortens the time taken for optical transformation, and enables the repeated use of an organic solution containing a enantioselective receptor, to thereby obtain optically pure amino acids in a simple and remarkably efficient manner, and to enable the very economical mass production of optically pure amino acids.

10 Claims, 2 Drawing Sheets

(56) References Cited

OTHER PUBLICATIONS

Sunil Kochhar et al., "Mechanism of racemization of amino acids by aspartate aminotransferase", European Journal of Biochemistry, 1992, pp. 563-569, vol. 203.

Gunter Helmchen et al., "Phosphinooxazolines—A New Class of Versatile, Modular P,N-Ligands for Asymmetric Catalysis", Accounts of Cemical Research, Nov. 3, 2000, pp. 336-345, vol. 33, No. 6.

Keiji Maruoka et al., "Enantioselective Amino Acid Synthesis by Chiral Phase-Transfer Catalysis", Chemical Reviews, Nov. 8, 2003, pp. 3013-3028, vol. 103, No. 8.

Hyunjung Park et al., "Bioinspired Chemical Inversion of L-Amino Acids to D-Amino Acids", JACS Communications, Nov. 1, 2007, pp. 1518-1519, vol. 129, No. 6.

Jik Chin et al., "Chiral Shift Reagent for Amino Acids Based on Resonance-Assisted Hydrogen Bonding", Organic Letters, 2004, pp. 2591-2593, vol. 6, No. 15.

Kwan Mook Kim et al., "Enantioselective Recognition of 1,2-Amino Alcohols by Reversible Formation of Imines with Resonance-Assisted Hydrogen Bonds", Organic letters, 2005, pp. 3525-3527, vol. 7, No. 16.

Lijun Tang et al., "Chirality conversion and enantioselective extraction of amino acids by imidazolium-based binol-aldehyde", Tetrahedron Letters, 2008, pp. 6914-6916, vol. 49.

Hyunjung Park et al., "Stereoconversion of Amino Acids and Peptides in Uryl-Pendant Binol Schiff Bases", Chemistry a European Journal, 2008 pp. 9935-9942, vol. 14.

Raju Nandhakumar et al., "Effects of ring substituents on enantioselective recognition of amino alcohols and acids in uryl-based binol receptors", Tetrahedron, 2008, pp. 7704-7708, vol. 64.

J. Olivard et al., "Catalytic Racemization of Amino Acids by Pyridoxal and Metal Salts." The Journal of Biological Chemistry, pp. 669-674, 1952.

* cited by examiner

METHOD FOR OBTAINING OPTICALLY PURE AMINO ACIDS

TECHNICAL FIELD

The present invention relates to a method of obtaining optically pure amino acids, using an extraction process including optical resolution and optical conversion.

BACKGROUND ART

Optically pure amino acids are used as ligands for asymmetric catalysts, or may be widely utilized as starting materials or intermediates necessary to synthesize a variety of medical products and physiologically active materials, and are thus regarded as very important from the industrial point of view (Helmchen, G.; Pfaltz, A. *Acc. Chem. Res.* 2000, 33, 336-345).

Amino acids are inexpensively and economically produced via fermentation. However, amino acids resulting from fermentation are limited to only the L-amino acids, for natural amino acids. Although optically pure D-amino acids and non-natural amino acids are produced via an enzyme process or an optical resolution process, they cost a lot to prepare and the prices thereof are therefore about 5~10 times higher than those of natural L-amino acids resulting from fermentation, and mass production thereof is difficult to achieve (Maruoka, K.; Ooi, T. *Chem. Rev.* 2003, 103, 3013).

The present inventors have developed a method of transforming L-amino acid into D-amino acid based on chirality of chiral aminoalcohol and amino acid via an imine bond using a binaphthol derivative having an aldehyde group as represented by the following chemical formula ((a) Park, H.; Kim, K. M.; Lee, A.; Ham, S.; Nam, W.; Chin, J. *J. Am. Chem. Soc.* 2007, 129, 1518-1519; (b) Kim, K. M.; Park, H.; Kim, H.; Chin, J.; Nam, W. *Org. Lett.* 2005, 7, 3525-3527).

[Binaphthol Derivative]

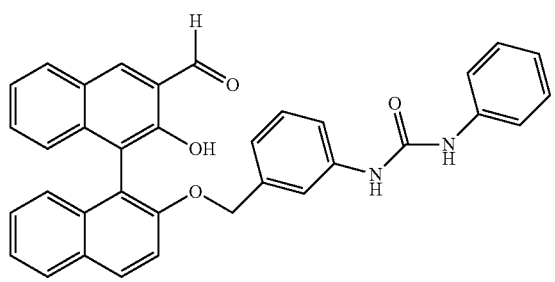 [SMILES: O=Cc1cc2ccccc2c(-c2c(OCc3cccc(NC(=O)Nc4ccccc4)c3)ccc3ccccc23)c1O]

The binaphthol derivative may enantioselectively react with amino acid to form an imine, and enables L-D optical transformation of amino acid in an organic solvent such as DMSO. As disclosed in previous patents and papers (Park, H.; Kim, K. M.; Lee, A.; Ham, S.; Nam, W.; Chin, J. *J. Am. Chem. Soc.* 2007, 129, 1518-1519), the L-D optical transformation method includes performing optical transformation in DMSO and then extracting the entire solution with water and an organic solvent. By this method, amino acid is transferred to a water layer and the binaphthol derivative is transferred to an organic layer, and the binaphthol derivative of the organic layer is recovered by removal of the organic solvent and can be re-used. In the case where the L-D optical transformation will be performed by means of the above method, a period of time required for optical transformation is about 24~48 hours. Because the DMSO solvent is freely miscible with both the water and the organic solvent, it is impossible to recover DMSO. Furthermore, DMSO must be completely removed from the organic layer in order to recover the binaphthol derivative. For this purpose, a large amount of water has to be used, and the working volume is increased, which undesirably decreases productivity. Also, the case where another solvent that is immiscible with water is used in lieu of DMSO is problematic because the reaction time of L-D optical transformation is further increased.

DISCLOSURE

Technical Problem

Accordingly, the present invention has been made keeping in mind the above problems occurring in the related art, and an object of the present invention is to provide a method of obtaining optically pure amino acids, which may drastically reduce the reaction time of optical transformation, and enables the repeated use of an organic solution containing a enantioselective receptor without the need to concentrate the organic solvent used, thus very efficiently and economically producing optically pure amino acids.

Technical Solution

An aspect of the present invention provides a method of obtaining optically pure amino acids using a basic aqueous solution containing an amino acid to be optically resolved or optically converted; an organic solution containing a enantioselective receptor that enantioselectively reacts with D- or L-amino acid to form an imine; and an acidic aqueous solution, the method comprising a first step of mixing the basic aqueous solution and the organic solution with stirring, and separating a basic aqueous solution layer and an organic solution layer; a second step of mixing the organic solution separated in the first step with the acidic aqueous solution with stirring, and separating an acidic aqueous solution layer and the organic solution layer; and a third step of recovering D- or L-amino acid from the acidic aqueous solution separated in the second step.

In this aspect, the method may further comprise repeating the first step and the second step one or more times using the basic aqueous solution separated in the first step and the acidic aqueous solution and the organic solution separated in the second step, before performing the third step.

In this aspect, the amino acid contained in the basic aqueous solution may be provided in the form of Li+, Na+ or K+ salt.

In this aspect, the basic aqueous solution may further comprise a racemization catalyst in order to achieve racemization of an amino acid. Also, in order to accelerate the racemization, the basic aqueous solution including the racemization catalyst may be heated to 50~100°, after which the first step may be performed.

In this aspect, an organic solvent contained in the organic solution may be a solvent mixture comprising an organic solvent which is immiscible with water and an organic solvent having a functional group with high polarity.

In this aspect, the organic solution may further comprise a phase transfer catalyst (PTC).

In this aspect, the amino acid may be α-amino acid or β-amino acid.

Another aspect of the present invention provides a method of accelerating racemization of an amino acid, comprising adding a racemization catalyst to a basic aqueous solution containing the amino acid, and heating the aqueous solution to 50~100°.

Advantageous Effects

According to the present invention, a method of obtaining optically pure amino acids can drastically reduce the reaction time of optical transformation, and can repetitively use an organic solution containing a enantioselective receptor without the need to concentrate the organic solvent used. Thus, optically pure amino acids can be very efficiently obtained using a simple process, and can be mass produced very economically.

BEST MODE

The present invention pertains to a method of obtaining optically pure amino acids using a basic aqueous solution containing an amino acid to be optically resolved or optically converted; an organic solution containing a enantioselective receptor which enantioselectively reacts with D- or L-amino acid to form an imine; and an acidic aqueous solution, the method comprising a first step of mixing the basic aqueous solution with the organic solution with stirring, and separating a basic aqueous solution layer and an organic solution layer; a second step of mixing the organic solution separated in the first step with the acidic aqueous solution with stirring, and separating an acidic aqueous solution layer and the organic solution layer; and recovering D- or L-amino acid from the acidic aqueous solution separated in the second step.

Before the third step, the method may further comprise repeating the first step and the second step one or more times using the basic aqueous solution separated in the first step and the acidic aqueous solution and the organic solution separated in the second step.

In the method according to the present invention, the term "optical resolution" means that mixed D- and L-amino acids are resolved into D-amino acid and L-amino acid, and the term "optical conversion" converts an L-amino acid into D-amino acid or a D-amino acid into L-amino acid thus obtaining an optically pure amino acid.

Figure 1:
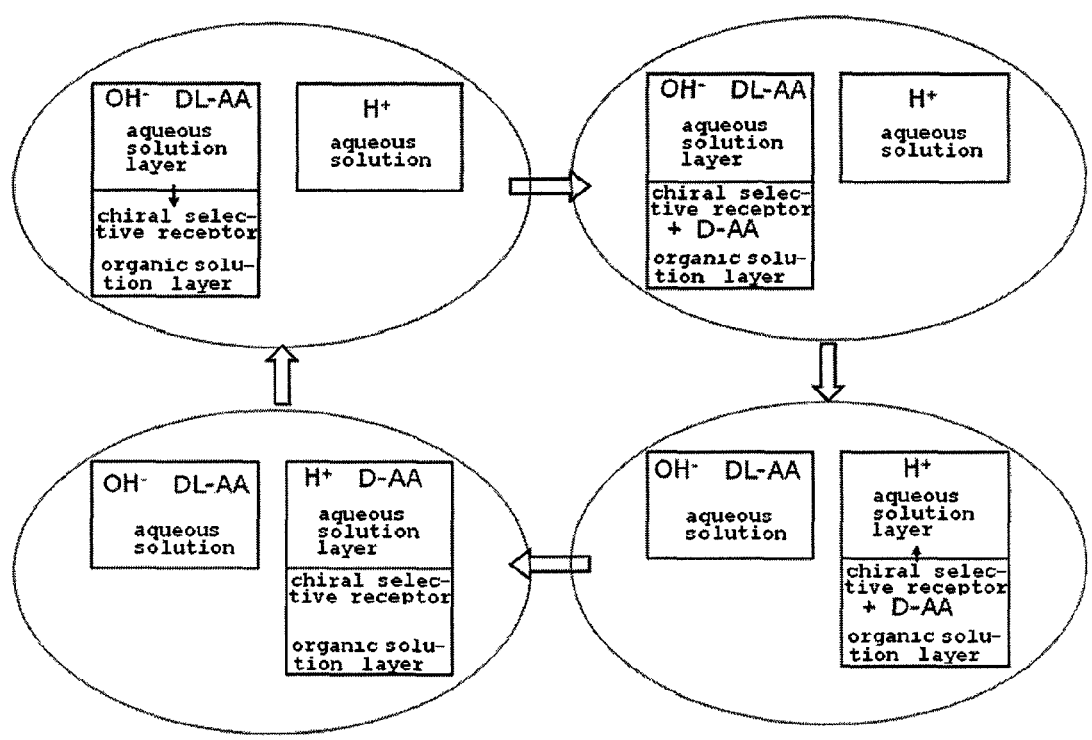
FIG. 1 is a schematic view showing a process according to the present invention.

In order to aid the understanding of the present invention, the method of obtaining optically pure amino acids is illustratively depicted in FIG. 1. As shown in FIG. 1, the organic solution plays a role in selectively sending D-amino acid among racemic amino acids (DL-amino acids) in the basic aqueous solution to the acidic aqueous solution while shuttling between the basic aqueous solution and the acidic aqueous solution. In this case, when racemization progresses in the basic aqueous solution, all of the amino acids contained in the basic aqueous solution are converted into D-amino acids, which are then transferred to the acidic aqueous solution. In the case where racemization does not occur in the basic aqueous solution, only D-amino acid contained in the basic aqueous solution is transferred to the acidic aqueous solution, so that the resolution of L-amino acid and D-amino acid takes place.

Below is a detailed description of the elements of the method according to the present invention.

1. Basic Aqueous Solution

In the present invention, the basic aqueous solution supplies an amino acid to be optically resolved or optically converted, and is prepared to exhibit basicity so that a enantioselective receptor contained in the organic solution efficiently reacts with the amino acid to form an imine bond. The basic aqueous solution may be typically prepared by dissolving a Li+, Na+ or K+ salt of amino acid in distilled water. The Li+, Na+ or K+ salt of the amino acid may be made by adding NaOH, KOH, etc. to an amino acid. As such, the molar amount of NaOH or KOH may be the same as or slightly more or less than that of the amino acid. This amount may be optimized to reflect the stability of amino acid, the degree of racemization, enantio-selectivity, etc. Furthermore, the basic aqueous solution may further include a racemization catalyst that racemizes the amino acid.

In the present invention, particularly useful is a racemization catalyst which is soluble in water but insoluble in an organic solvent.

The racemization catalyst may include a salicylaldehyde derivative. Such a salicylaldehyde derivative has —OH group and an aldehyde group (—CHO) which are adjacent to each other, and thus may form a stable imine bond (—CH=N—) with an amino acid, thereby inducing racemization of an amino acid. Examples of the salicylaldehyde derivative may include PLP (pyridoxal-5'-phosphate), pyridoxal, etc., which may be used alone or in combinations of two or more. Particularly useful as the racemization catalyst is PLP (pyridoxal-5'-phosphate).

The amount of the racemization catalyst is the most appropriate when being 5% of the mol of the amino acid, but may vary depending on the kind of amino acid.

2. Organic Solution

In the present invention, the organic solution contains the enantioselective receptor dissolved therein. The enantioselective receptor refers to a compound that enantioselectively reacts with an amino acid to form an imine. For example, in the case where the enantioselective receptor is of the S-form, it may be enantioselective for D-amino acid. Whereas, in the case where the enantioselective receptor is of the R-form, it may be enantioselective for L-amino acid. However, such chiral selectivity may vary depending on the kind of compound.

In the present invention for example when an S-enantioselective receptor is dissolved in the organic solution layer, D-amino acid among racemic amino acids in the basic aqueous solution layer may be transferred to the organic solution layer while selectively reacting with the S-enantioselective receptor to form an imine.

In the present invention, the enantioselective receptor may be used without limitation so long as it may enantioselectively react with the amino acid to form an imine and thus may transfer the amino acid from the aqueous solution layer to the organic solution layer. In particular, any derivative having a salicylaldehyde group able to form an imine with an amino acid may be used in the method according to the present invention so long as it is enantioselective. Even when the compounds provided do not have salicylaldehyde, they may be used without limitation in the present invention so long as they have chiral selectivity for amino acids and satisfy the above requirements.

It is preferred that a enantioselective receptor which is insoluble in water but soluble in an organic solvent be used.

The enantioselective receptor usable in the present invention may include for example compounds represented by Chemical Formulas 1 and 2 below.

[Chemical Formula 1]

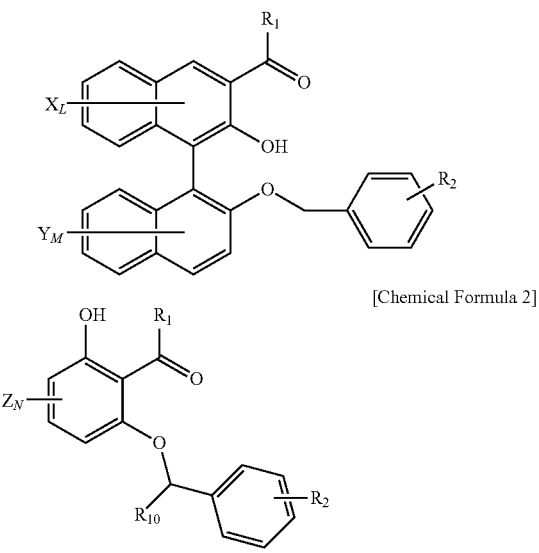

[Chemical Formula 2]

In Chemical Formulas 1 and 2, X is independently selected from the group consisting of hydrogen; halogen; amino; nitro; cyano; formyl; carboxyl; C1~C10 alkyl substituted or unsubstituted with one or more substituents selected from the group consisting of halogen, hydroxyl, amino, cyano, nitro, and C6~C10 aryl; C1~C10 alkylcarbonyl; C6~C10 aryl; and C1~C10 alkoxy;

Y is independently selected from the group consisting of hydrogen; halogen; amino; nitro; cyano; formyl; carboxyl; C1~C10 alkyl substituted or unsubstituted with one or more substituents selected from the group consisting of halogen, hydroxyl, amino, cyano, nitro, and C6~C10 aryl; C1~C10 alkylcarbonyl; C6~C10 aryl; and C1~C10 alkoxy;

Z is independently selected from the group consisting of hydrogen; halogen; amino; nitro; cyano; formyl; carboxyl; C1~C10 alkyl substituted or unsubstituted with one or more substituents selected from the group consisting of halogen, hydroxyl, amino, cyano, nitro, and C6~C10 aryl; C1~C10 alkylcarbonyl; C6~C10 aryl; and C1~C10 alkoxy;

L is an integer of 0~5, M is an integer of 0~5, and N is an integer of 0~3;

R1 is hydrogen; tosyl; $CH_3SO_2$—; $CH_3CO$—; C1~C10 alkyl substituted or unsubstituted with one or more substituents selected from the group consisting of halogen and OH; C4~C10 cycloalkyl substituted or unsubstituted with one or more substituents selected from the group consisting of halogen and OH; C4~C10 cycloalkenyl substituted or unsubstituted with one or more substituents selected from the group consisting of halogen and OH; C4~C10 cycloalkynyl substituted or unsubstituted with one or more substituents selected from the group consisting of halogen and OH; or C6~C12 aryl substituted or unsubstituted with one or more substituents selected from the group consisting of halogen, OH and C1~C5 alkyl;

R2 is —NHCX'R3, —NHS(=O)$_a$R3,

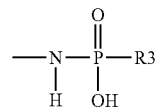

or —NHC(NHR5)$^+$R4, wherein X' is oxygen or sulfur, a is 1 or 2, R3 and R4 are each independently hydrogen; C1~C10 alkyl substituted or unsubstituted with halogen; —NR6R7; or OR8, R5 to R8 are each independently hydrogen; C1~C10 alkyl substituted or unsubstituted with halogen; or C6~C12 aryl substituted or unsubstituted with one or more substituents selected from the group consisting of halogen, nitro, C1~C5 alkyl, C1~C5 alkoxy and C1~C5 perfluoroalkyl, and R5 and R6 may be linked to form a ring, wherein when R2 is —NHC(NH$_2$)NH$_2^+$ or —NHCHNH$_2^+$, the counter ion is a halogen ion or R9COO$^-$, R9 is C6~C12 aryl substituted or unsubstituted with C1~C10 alkyl or C1~C5 alkyl; and R10 is hydrogen; C1~C10 alkyl substituted or unsubstituted with one or more substituents selected from the group consisting of halogen and OH; C4~C10 cycloalkyl substituted or unsubstituted with one or more substituents selected from the group consisting of halogen and OH; C4~C10 cycloalkenyl substituted or unsubstituted with one or more substituents selected from the group consisting of halogen and OH; C4~C10 cycloalkynyl substituted or unsubstituted with one or more substituents selected from the group consisting of halogen and OH; or C6~C12 aryl substituted or unsubstituted with one or more substituents selected from the group consisting of halogen, OH, C1~C5 alkyl, and C1~C5 alkoxy, wherein the alkyl refers to a linear or branched alkyl group.

In the compound represented by Chemical Formula 2, carbon linked with R10 may be of the R- or S-form.

Specific examples of the compounds represented by Chemical Formulas 1 and 2 are illustrated below.

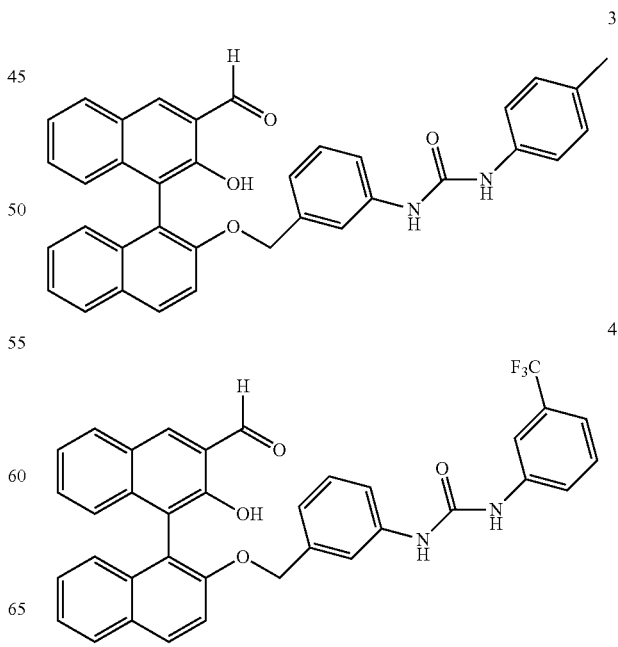

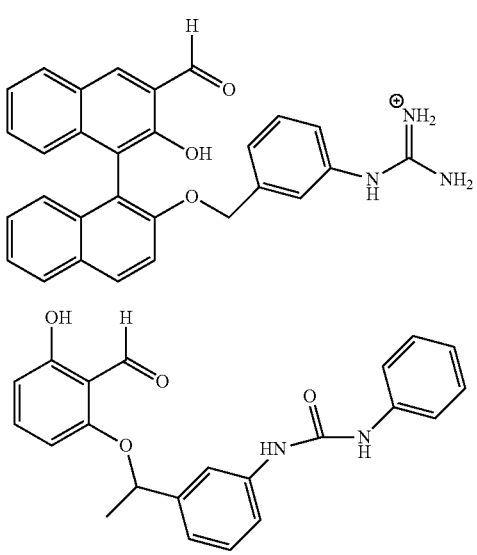

Compounds 3, 4 and 5 have a binaphthol-3-formyl-2-hydroxyl group in common, and Compound 6 is a derivative of a salicyl compound. Compounds 3, 4, 5 and 6 may be prepared according to the methods disclosed in published papers and patents ((a) Nandhakumar, R; Ryu, J.; Park, H.; Tang, L.; Choi, S.; Kim, K. M. Tetrahedron 2008, 64, 7704.; (b) Kim, K. M.; Nam, W.; Park, H.; Chin, J. U.S. Pat. No. 7,268,252 B2; (c) Kim, K. M.; Tang, L. US 2009/0023931 A1). In addition to the above compounds, the other compounds disclosed in the above papers and patents may be used in the present invention.

Also, the organic solution may include a phase transfer catalyst (PTC) so that the amino acid of the basic aqueous solution is easily transferred to the organic solution layer.

Examples of the PTC include a quaternary ammonium salt, a phosphonium salt, etc., which are widely used. Particularly useful in the present invention is Aliquat 336 (Tricaprylylmethylammonium chloride) which is not insoluble in the aqueous solution layer. Preferably, molar amount of PTC is the same as that of enantioselective receptor, but may be adjusted slightly more or less in consideration of chiral selectivity and the reaction time to form an imine.

The organic solvent used to prepare the organic solution includes a solvent which is immiscible with water. Examples thereof include chloroform, methylenechloride (MC), ethylacetate (EA), toluene, 2-pentanone, butyronitrile, tolunitrile, methylisobutylketone and mixtures thereof. In order to increase chiral selectivity, particularly useful is a mixture comprising an organic solvent having a highly polar group such as nitrile, carbonyl, sulfoxide or the like and an organic solvent that is immiscible with water. When the organic solvent having a highly polar group such as nitrile, carbonyl, sulfoxide or the like is used alone, chiral selectivity is increased but this solvent may partially be dissolved in water. Hence, when this solvent is used together with the solvent that is immiscible with water, water-miscibility may be prevented while increasing the selectivity. The organic solvent that is immiscible with water and the organic solvent having a functional group with high polarity may be mixed at a volume ratio of 1:9~9:1.

Examples of the solvent mixture include a mixture of methylene chloride and butyronitrile, a mixture of chloroform and tolunitrile, etc.

3. Acidic Aqueous Solution

The acidic aqueous solution is prepared to remove the amino acid from an imine formed via the reaction of the amino acid and the enantioselective receptor in the organic solution. The acidic aqueous solution may be prepared using a variety of acids. For example, an acidic solution may be prepared by the addition of HCl. The appropriate concentration is determined by considering the kind of amino acid and the reaction time to hydrolyze the imine bond, etc.

4. Principle of the Method According to the Invention

The organic solution and the basic aqueous solution of the amino acid are not mixed with each other. When these two layers are stirred together using a typical method, only one form (D-form or L-form) of amino acid of the basic aqueous solution, which is able to form a bond with the enantioselective receptor (S-form or R-form) in the organic solution, selectively reacts with the enantioselective receptor to form an imine. For example, in the case where the enantioselective receptor is of the S-form, it selectively reacts with D-amino acid to form an imine. After the enantioselective formation of the imine is completed, the organic solution layer is separated and then stirred along with the acidic aqueous solution that resolves the amino acid. As such, because the acidic aqueous solution is acidic, the amino acid is transferred to the aqueous solution layer while breaking the imine of the organic solution layer. The original enantioselective receptor remains in the organic solution layer, and thus such an organic solution is used as it is and the above procedures may be repetitively performed. As such, in the case where amino acid is continuously racemized in the basic aqueous solution, all of the DL-amino acids are transformed into D-amino acids which are then transferred to the acidic aqueous solution. Alternatively, even when L-amino acid in lieu of DL-amino acids is added to the basic aqueous solution, they are immediately racemized, and the same results as in the addition of DL-amino acids are obtained. In the method according to the present invention, the period of time required to enantioselectively transfer amino acid from the basic aqueous solution layer to the organic solution layer is 2~3 hours, and the racemization of amino acid in the basic aqueous solution may also be carried out for a short period of time using an appropriate catalyst, and thus the total L-D optical transformation of amino acid may be completed within a short period of time. According to the method in the known patents, when optical transformation is carried out in DMSO, all of the procedures including reaction and recovery require at least several days. Hence, the method according to the present invention is regarded as very outstanding. Furthermore, in the present invention, the organic solution layer of the enantioselective receptor may be re-used directly without additional purification, which is very economic.

5. Racemization of Amino Acid in Basic Mucous Solution

In the basic aqueous solution that supplies the amino acid, racemization catalyst such as PLP(pyridoxal phosphate) may be added. In the basic aqueous solution, PLP forms an imine with amino acid and racemizes amino acid. The amount of the PLP is preferably 5 mole % of the amino acid but may vary depending on the kind of amino acid. The racemization of amino acid at 5 mole % PLP slowly occurs at room temperature and thus reaches about 30% for a week. This may be checked by adding for example a Na+ salt of phenylalanine with 5 mole % PLP in $D_2O$ and then observing the degree of deuteration of α-hydrogen. Here, the degree of deuteration of α-hydrogen indicates the racemization of the amino acid. Even when the amount of the PLP is increased to 20 mole %, the rate of racemization of the amino acid is not increased. However, when the temperature of the aqueous solution is increased to 50~100° in the present invention, the racemization of the amino acid may take place within the short period of time of 1 hour. Thus, in order to rapidly perform the racemization in the basic aqueous solution that supplies the amino acid, the temperature of the basic aqueous solution may be increased to the above range. When the temperature of the aqueous solution is heated to the level below 50°, the effect of accelerating the racemization is insignificant, and the aqueous solution can not be heated to higher temperature than 100°. When the amino acid of the basic aqueous solution layer is transferred to the organic solution layer, amino acid is continuously added so that optical transformation may continue.

6. Principle of Chiral Selectivity, Principle of Chiral Conversion, and Scope of the Invention The chiral selectivity in the present invention is based on the structural stability of an imine, the detailed principle of which is disclosed in a variety of papers. In the published papers (JACS 2007; Che. Eur. J. 2008; Tetrahedron 2008), chiral conversion of amino acid is described using binaphtholaldehyde or other derivatives in a DMSO solvent. Generally, in the organic solvents used in the method according to the present invention, chiral conversion of the amino acid does not easily occur. However, this invention provides the method to enable the chiral conversion of all DL-amino acids. This is because the racemization of an amino acid is carried out in the basic aqueous solution. Specifically, the chiral conversion of all DL-amino acids is rendered possible by the combination of racemization in the basic aqueous solution and the enantioselective transfer of amino acid from the basic aqueous solution layer to the organic solution layer, which is evaluated to be very superior, compared to typical optical resolution the maximum yield of which is only 50%.

In the method according to the present invention, chiral conversion may be applied to any α-amino acid which may be racemized in an aqueous solution in principle. Also the method according to the present invention may be effectively applied to chiral separation of β-amino acid. In the same principle, the method according to the present invention may be applied to all of amines able to form an imine with a enantioselective receptor.

In addition, the present invention pertains to a method of accelerating racemization of an amino acid, comprising adding a racemization catalyst to the basic aqueous solution containing the amino acid, and then heating the aqueous solution to 50~100°.

As mentioned above, in the racemization of the amino acid, even when the amount of the racemization catalyst is increased up to 20%, the rate of racemization of amino acid is not increased. However, in the present invention, when the racemization catalyst is added and the temperature of the aqueous solution is increased to 50~100°, the racemization of the amino acid may be completed within the short period of time of 1 hour. Thus, in order to rapidly perform racemization in an aqueous solution that supplies the amino acid, the temperature of the aqueous solution is preferably heated to the above range.

The racemization catalyst may include a salicylaldehyde derivative. The salicylaldehyde derivative has —OH group and the aldehyde group (—CHO) adjacent to each other and may form a stable imine bond (—CH=N—) with the amino acid, thereby inducing the racemization of the amino acid. The salicylaldehyde derivative may include PLP (pyridoxal phosphate), pyridoxal, etc., which may be used alone or in combinations of two or more. Particularly useful as the racemization catalyst is PLP (pyridoxal-5'-phosphate).

The pH of the basic aqueous solution is 14 or less but exceeding 7, and preferably in the range of 10~12.

MODE FOR INVENTION

The following examples which are set forth to illustrate but are not to be construed as limiting the present invention, may provide a better understanding of the present invention, and may be appropriately modified or varied by those skilled in the art within the scope of the present invention.

Example 1

Preparation of Enantioselective Receptor

[Compound 3]

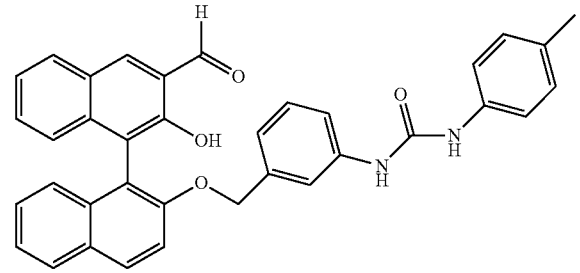 [SMILES: Cc1ccc(NC(=O)Nc2cccc(COc3ccc4ccccc4c3-c3c(O)c(C=O)cc4ccccc34)c2)cc1]

Compound 3 was synthesized according to the synthesis method of Compound 1 disclosed in the published paper (Park, H.; Nandhakumar, R.; Hong, J.; Ham, S.; Chin, J. Kim, K. M. Chem. Eur. J. 2008, 14, 9935). When Compound 3 was synthesized, 4-methylphenylisocyante was used instead of phenylisocyanate used upon synthesis of Compound 1 in the above paper.

Compound 3: $^1$H NMR (CDCl3, 250 MHz): δ(ppm)=10.5 (s, 1H), 10.2 (s, 1H), 8.3 (s, 1H), 6.5-8.1 (m, 20H), 5.1 (dd, 2H), 2.3 (s, 3H).

Example 2

Preparation of Organic Solution

Compound 3 (10.0 g, 18 mmol, S-optical isomer) as a enantioselective receptor and Aliquot 336 (10.0 g, 18 mmol) as PTC (Phase Transfer Catalyst) were dissolved in a solvent mixture of CDCl$_3$ (50 ml) and toluene-4-nitrile (50 ml) at 1:1, thus preparing an organic solution.

Example 3

Preparation of Basic Aqueous Solution

Phenylalanine (racemic form, 30 g, 180 mmol) and 1.0 equivalent of NaOH were sequentially added to water (100 ml) and completely dissolved therein, after which 1.5 g of PLP was added thereto, thus preparing a basic aqueous solution.

Example 4

Preparation of Acidic Aqueous Solution

Concentrated hydrochloric acid (10 g) was diluted 10 folds thus preparing 100 ml of an acidic aqueous solution.

Example 5

Optically Selective Transfer of Phenylalanine

Figure 2:
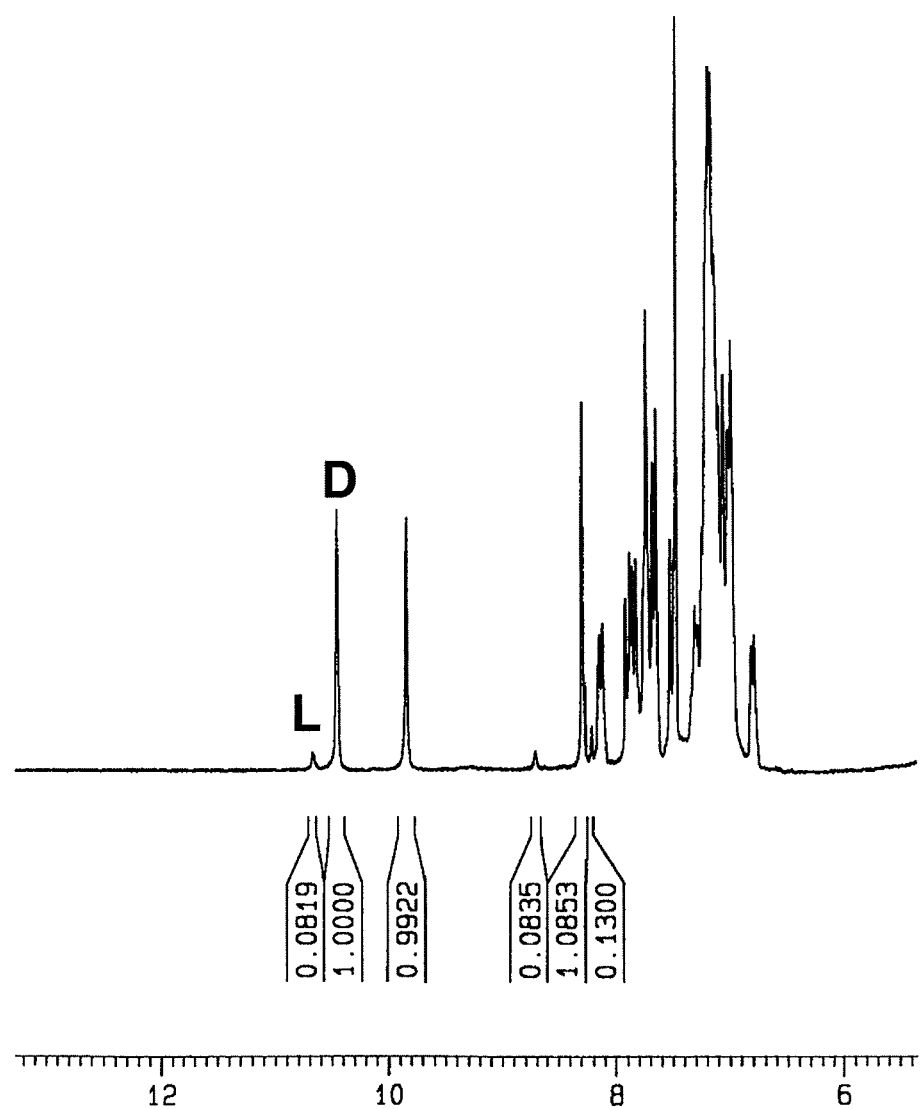
FIG. 2 is a $^1$H NMR spectrum showing the chiral selectivity of an imine formed via bonding of an amino acid and a enantioselective receptor in Example 5 according to the present invention.

The organic solution and the basic aqueous solution prepared as above were placed in a 2 L round-bottom flask and then stirred for 2 hours 30 minutes. Whether an imine was formed was checked from a portion of the organic solution layer using $^1$H NMR (FIG. 2). As a result, Compound 3 was completely used to enantioselectively form an imine with the amino acid. The chiral selectivity was determined via integration of uryl-NH signal of Compound 3. As a result, the chiral selectivity was about L:D=1:12. In FIG. 2, the small peak represented by L is for NH of an imine formed with L-phenylalanine and the peak represented by D is for NH of an imine formed with D-phenylalanine.

Such chiral selectivity was the same as chiral selectivity upon optical transformation from L-phenylalanine into D-phenylalanine in DMSO (Park, H.; Kim, K. M.; Lee, A.; Ham, S.; Nam, W.; Chin, J. J. Am. Chem. Soc. 2007, 129, 1518-1519). The organic solution layer was separated from the aqueous solution layer using a separatory funnel, and then stirred together with the acidic aqueous solution for 1 hour. Thereafter, as a result by $^1$H NMR, all amino acids were separated from Compound 3, and in the organic solution layer, Compound 3 and Aliquat 336 were present in the same state as before optical transformation. Also, the acidic aqueous solution layer had D-phenylalanine separated from the organic solution layer and transferred thereto.

Using the basic aqueous solution, the organic solution and the acidic aqueous solution which were subjected to optically selective transfer one time as above, the same procedures as above were repeated two times. Whenever the test was repeated, added to the basic aqueous solution were 2.97 g (18 mmol) of racemic phenylalanine and the same molar amount of NaOH so that a predetermined molar amount of phenylalanine was kept in the basic aqueous solution. The chiral selectivity in the second and third repetition tests was slightly smaller than in the first test. This is considered to be because a proportion of L-phenylalanine was slightly increased in the basic aqueous solution due to the optically selective transfer that took place.

The proportion of L-form was increased in the phenylalanine of the basic aqueous solution, and thus the aqueous solution layer was heated and stirred at 900 for 1 hour so that racemization occurred, followed by repeating the same test as above. The chiral selectivity of phenylalanine transferred to the organic solution from the basic aqueous solution in which racemization had occurred was the same as in the first test results.

Thereafter, the test was repeated in the same manner as above, so that a total of thirty tests were performed. During the repeated tests, concentrated hydrochloric acid was added so that the pH of the acidic aqueous solution was always maintained at 1~2. Also, the pH of the basic aqueous solution was set to 12.0 by adjusting the amount of added NaOH taking into consideration the introduction of HCl via the organic solution layer from the acidic aqueous solution. $^1$H NMR measurement taken for all thirty tests revealed that the chiral selectivity was almost the same for every test. After the repetition of thirty tests had completed, $^1$H NMR of the organic solution layer recovered after separating phenylalanine from the acidic aqueous solution layer was the same as that of initial organic solution.

Example 6

Recovery of Phenylalanine from Acidic Aqueous Solution Layer

After the repetition of thirty tests in Example 5, NaOH was added to the acidic aqueous solution layer so that the pH thereof was adjusted to 7.0. Then, phenylalanine was precipitated, recovered, washed three times with cold water, and dried at 500 under reduced pressure. The dried phenylalanine had a weight of 84 g and a total recovery of 94%. The results of analyzing the dried phenylalanine with HPLC showed that D-form was 92% with the remainder being L-form.

Example 7

Test for Increase in Optical Purity of Phenylalanine 10 g (50 mmol) of the phenylalanine (D-form 92%) obtained in Example 6 was dissolved in 100 ml of water, and 4.0 g (100 mmol) of NaOH was slowly added thereto thus preparing a phenylalanine salt. This aqueous solution was mixed with a solution mixture of $CDCl_3$/toluene-4-nitrile (volume 1:1) having Compound 3 (3 g, 5.4 mmol) as an R-optical isomer and Aliquat (3 g, 5.4 mmol) dissolved therein, and then stirred for 5 hours. As a result of analyzing the organic solution layer via $^1$H NMR, an imine was formed from L-phenylalanine and Compound 3. The organic solution layer was separated and stirred together with an HCl aqueous solution for 1 hour so that the L-phenylalanine of the organic solution layer was transferred to the HCl aqueous solution layer. The HCl aqueous solution layer was made under the same conditions as in Example 4. The organic solution layer separated from the HCl aqueous solution layer was transferred again to the basic aqueous solution layer having concentrated D-phenylalanine, after which the same test was performed once more. After the same two tests were performed, the amount of Compound 3 as the R-optical isomer of the organic solution layer was decreased to ½, after which the same test was repeated four times. HCl was added to the basic aqueous solution layer having concentrated D-phenylalanine so that the pH thereof was adjusted to 7.0. The neutral phenylalanine precipitation was filtered, washed three times with cold water, and then dried at 50° under reduced pressure. The D-form of the dried phenylalanine was measured to be 99.7% via HPLC and weighed 6.2 g.

Example 8

Racemization in Amino Acid Aqueous Solution

DL-phenylalanine (1.0 g) and PLP (50 mg) were added to $D_2O$ (5 ml), after which a NaOH aqueous solution was added thereto while being stirred so that all components were dissolved. The results of observation by $^1$H NMR at room temperature showed that α-hydrogen of the phenylalanine was substituted with D. However, the substitution rate was slow, and after 1 week, the substitution with D occurred at only about 30%. Also, the amount of the PLP was changed. Specifically, when the amount of the PLP was increased, the rate of substitution with D was decreased instead, and even when the amount of the PLP was 5% or less of the mol of the DL-phenylalanine, the substitution rate was decreased. Only a small amount of substitution with D occurred after 1 week in the absence of the PLP. In addition, when the temperature of the $D_2O$ solution under the same conditions was increased to 70° or more, the substitution with D took place at a very fast rate, and the substitution with D was completed within 30 minutes at 80° or more. The substitution with D indicates racemization of the amino acid, and thus these test results reveal that racemization was taking place.

The other amino acids, for example, serine, methionine, valine, leucine, tryptophan, and tyrosine, were subjected to the same test, and the same results were obtained. In the case of valine, the racemization rate took 2~3 times longer than the other amino acids.

Example 9

Optically Selective Transfer for Other Amino Acids

α-amino acids, such as DL-serine, DL-alanine, DL-valine, DL-leucine, and DL-tryptophan, and β-amino acids such as DL-3-aminobutyric acid, β-phenylalanine, β-leucine, β-homophenylalanine, β-homoleucine and 3-aminoisobutyric acid were subjected to optically selective transfer test in the same manner as in Example 5. The chiral selectivity of the amino acid transferred from the aqueous solution layer to the organic solution layer was determined by the calculation of the area of the $^1$H NMR peak. The results are shown in Table 1 below.

TABLE 1

| α-Amino acid | Selectivity (D-AA/L-AA) | β-Amino acid | Selectivity |
|---|---|---|---|
| Alanine | 7/1 | 3-aminobutyric acid | 4/1 |
| Serine | 9/1 | β-phenylalanine | 20/1 |
| Valine | 12/1 | β-leucine | 17/1 |
| Leucine | 16/1 | β-homophenylalanine | 14/1 |
| Phenylalanine | 12/1 | β-homoleucine | 11/1 |
| Tryptophan | 10/1 | 3-aminoisobutyric acid | 1/1 |

As is apparent from the results of Table 1, the method according to the present invention shows high chiral selectivity for valine which is an α-amino acid. The valine may be racemized in the aqueous solution layer, and thus the method according to the present invention can be effectively applied to the chiral conversion of the amino acid such as valine. As disclosed in the published papers (JACS 2007; Che. Eur. J. 2008), when chiral conversion is performed using a DMSO solvent, chiral conversion for valine cannot be carried out. However, because chiral conversion for valine was successfully performed by the method according to the present invention, these results can be recognized as a drastic advancement in the art.

Also as is apparent from Table 1, the method according to the present invention can exhibit a relatively high chiral selectivity for β-phenylalanine, β-leucine, β-homophenylalanine, β-homoleucine among β-amino acids. Thus, the method according to the present invention can be usefully applied to the optical resolution of these β-amino acids. In the case of β-amino acid, racemization does not occur in the aqueous solution layer, and thus the method according to the present invention can be applied not to chiral conversion but to the separation of chiral isomers for β-amino acid.

The invention claimed is:

1. A method of obtaining optically pure amino acids using a basic aqueous solution containing an amino acid to be optically resolved or optically converted; an organic solution containing a stereo-selective receptor that enantioselectively reacts with D- or L-amino acid to form an imine; and an acidic aqueous solution, the method comprising:
a first step of mixing the basic aqueous solution and the organic solution with stirring, and separating a basic aqueous solution layer and an organic solution layer;
a second step of mixing the organic solution separated in the first step with the acidic aqueous solution with stirring, and separating an acidic aqueous solution layer and the organic solution layer; and
a third step of recovering D- or L-amino acid from the acidic aqueous solution separated in the second step;
wherein the stereo-selective receptor is a compound represented by Chemical Formula 1 below:

Chemical Formula 1

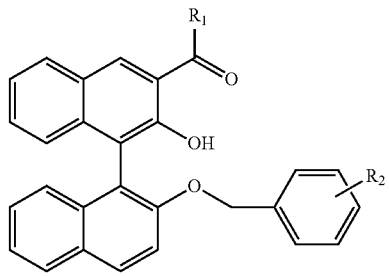

wherein, R1 is hydrogen; C1~C10 alkyl substituted or unsubstituted with one or more substituents selected from the group consisting of halogen and OH; C4~C10 cycloalkyl substituted or unsubstituted with one or more substituents selected from the group consisting of halogen and OH; or C6~C12 aryl substituted or unsubstituted with one or more substituents selected from the group consisting of halogen and OH;
R2 is —NHCX'R3, wherein X' is oxygen or sulfur;
R3 is —NR6R7; R6 and R7 are each independently hydrogen; C1~C10 alkyl substituted or unsubstituted with halogen; C6~C12 aryl substituted or unsubstituted with halogen; or C1~C5 alkyl and C1~C5 perfluoroalkyl; and
wherein, the organic solution further comprises a phase transfer catalyst (PTC).

2. The method of claim 1, further comprising repeating the first step and the second step one or more times using the basic aqueous solution separated in the first step and the acidic aqueous solution and the organic solution separated in the second step, before performing the third step.

3. The method of claim 1, wherein the amino acid contained in the basic aqueous solution is provided in a form of Li+, Na+ or K+ salt of amino acid.

4. The method of claim 1, wherein the basic aqueous solution further comprises a racemization catalyst that racemizes the amino acid, wherein the racemization catalyst comprises one or more compounds selected from the group consisting of PLP (pyridoxal phosphate) and pyridoxal.

5. The method of claim 4, wherein in order to accelerate racemization of the amino acid, the basic aqueous solution is heated to 50~100° C., after which the first step is performed.

6. The method of claim 1, wherein an organic solvent contained in the organic solution is a solvent mixture comprising an organic solvent which is immiscible with water and an organic solvent having a functional group having high polarity.

7. The method of claim 6, wherein the solvent mixture is a solvent mixture of methylenechloride and butyronitrile or a solvent mixture of chloroform and tolunitrile.

8. The method of claim 1, wherein the acidic aqueous solution is an HCl aqueous solution.

9. The method of claim 1, wherein the amino acid is α-amino acid.

10. The method of claim 1, wherein the stereo-selective receptor is selected from the group consisting of compounds represented by Chemical Formulas 3 and 4 below:

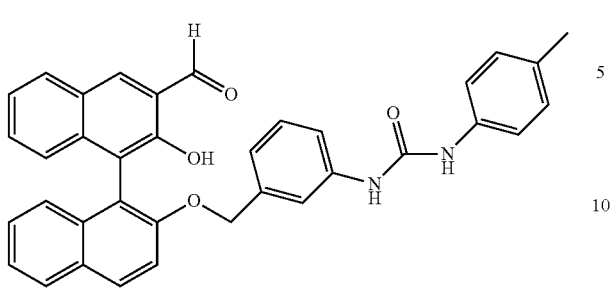
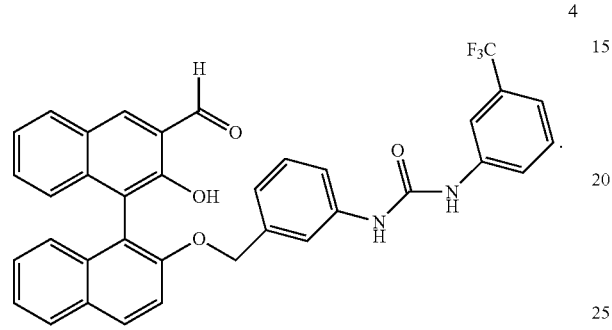
* * * * *